United States Patent [19]
Vogelstein et al.

[11] Patent Number: 5,882,865
[45] Date of Patent: Mar. 16, 1999

[54] CANCER DRUG SCREEN BASED ON CELL CYCLE UNCOUPLING

[75] Inventors: Bert Vogelstein, Baltimore; Todd Waldman, Bethesda; Christoph Lengauer, Columbia; Kenneth W. Kinzler, BelAir, all of Md.

[73] Assignee: The Johns Hopkins University, Baltimore, Md.

[21] Appl. No.: 781,201

[22] Filed: Jan. 10, 1997

Related U.S. Application Data

[62] Division of Ser. No. 620,340, Mar. 22, 1996.

[51] Int. Cl.$^6$ ................ C12Q 1/68; C12N 5/08
[52] U.S. Cl. ................................ 435/6; 435/366
[58] Field of Search ............ 435/5, 6, 7.1, 177.3, 435/366

[56] References Cited

PUBLICATIONS

Waldman et al. Cancer Research, vol. 55, pp. 5187–5190 (Nov. 15, 1995).
Brugarolas, "Radiation–induced Cell Cycle Arrest Compromised By p21 Deficiency," *Nature* 377:522–557 (1995).
Deng, "Mice Lacking p21$^{CIP1/WAF1}$ Undergo Normal Development, But Are Defective in G1 Checkpoint Control," Cell, 82:675–684 (1959).
Gao, "Somatic Mutations of the WAF1/CIP1 Gene in Primary Prostate Cancer," *Oncogene*, 11, 1395–1398 (1995).
Gorczyca, "Detection of DNA Strand Breaks in Individual Apoptotic Cells by the in Situ Terminal Deoxynucleodidyl Transferase and Nick Translation Assays," *Cancer Research*, 53:1945–1951 (1993).
Hotz, Changes in Nuclear Chromating Related in Apoptosis or Necrosis Induced by the DNA Topoisomerase II Inhibitor Fostriecin in MOLT–4 and HL–60 Cells are Revealed by Altered DNA Sensitivity to Denaturation, *Exp. Cell Research*, 201:184–191 (1992).
Hunter, Cyclins and CancerII: Cyclin D and CDK Inhibitors Come of Age, *Cell*, 79:573–582 (1994).
Kung, "Cell Line–Specific Differences in the Control of Cell Cycle Progression in the Absence of Mitosis," *Cell Biology*, 87:9553–9557.
Sheer, "Inhibitors of Mammalian G, Cyclin–Dependent Kinaser," *Genes & Development*, 9:1149–1163 (1995).
Swat, "Detection of Apoptosis of Immature CD4+8+Thymocytes by Flow Cytometry," *J. Immunol, Meth.* 137:79–87 (1991).
Woods, "Taxol–Induced Mitotic Block Triggers Rapid Onset of a p53–Independent Apoptotic Pathway," Molecular Medicine, 1:506–526 (1995).

*Primary Examiner*—James Ketter
*Assistant Examiner*—Irem Yucel
*Attorney, Agent, or Firm*—Banner & Witcoff, Ltd.

[57] ABSTRACT

Checkpoint gene-defective human cells are useful for screening potential anti-tumor agents. Potential therapeutic agents are screened for the ability to cause DNA accumulation or cell death in a checkpoint gene-defective human cell.

12 Claims, 5 Drawing Sheets

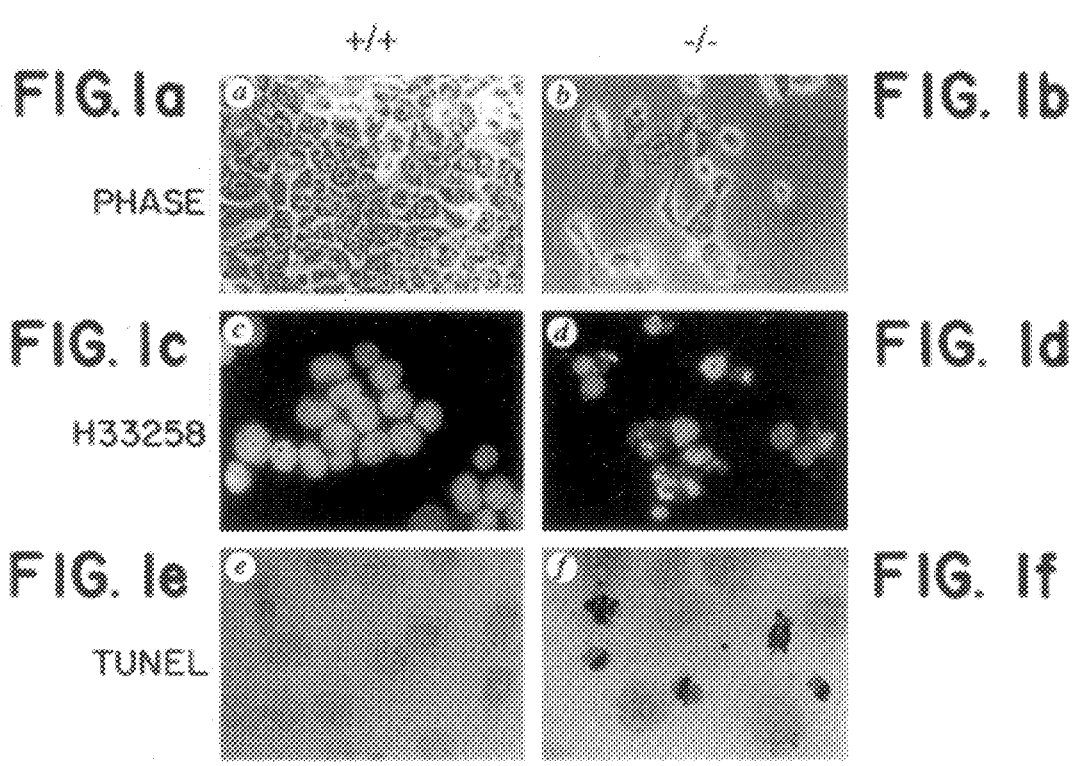

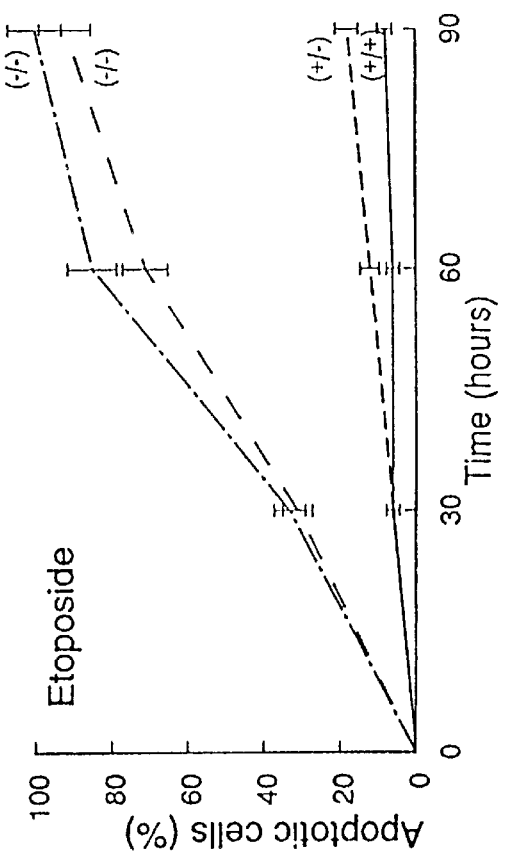
FIG. 2a
FIG. 2b
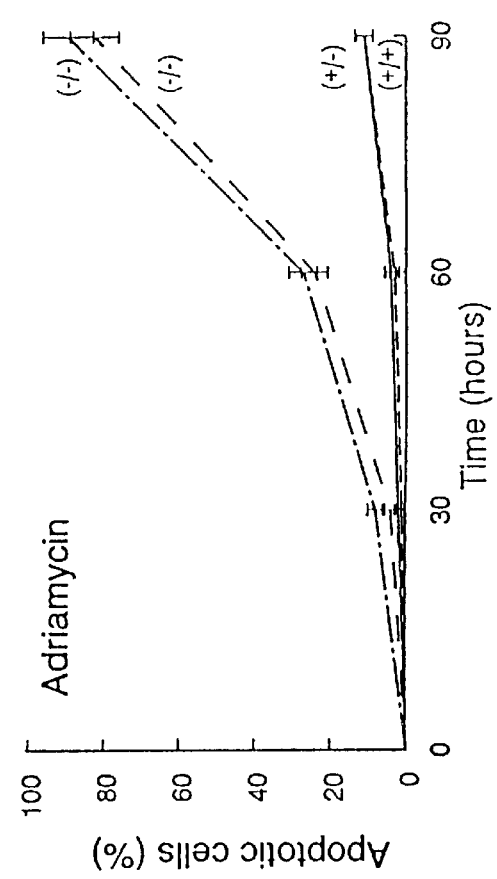
FIG. 2c
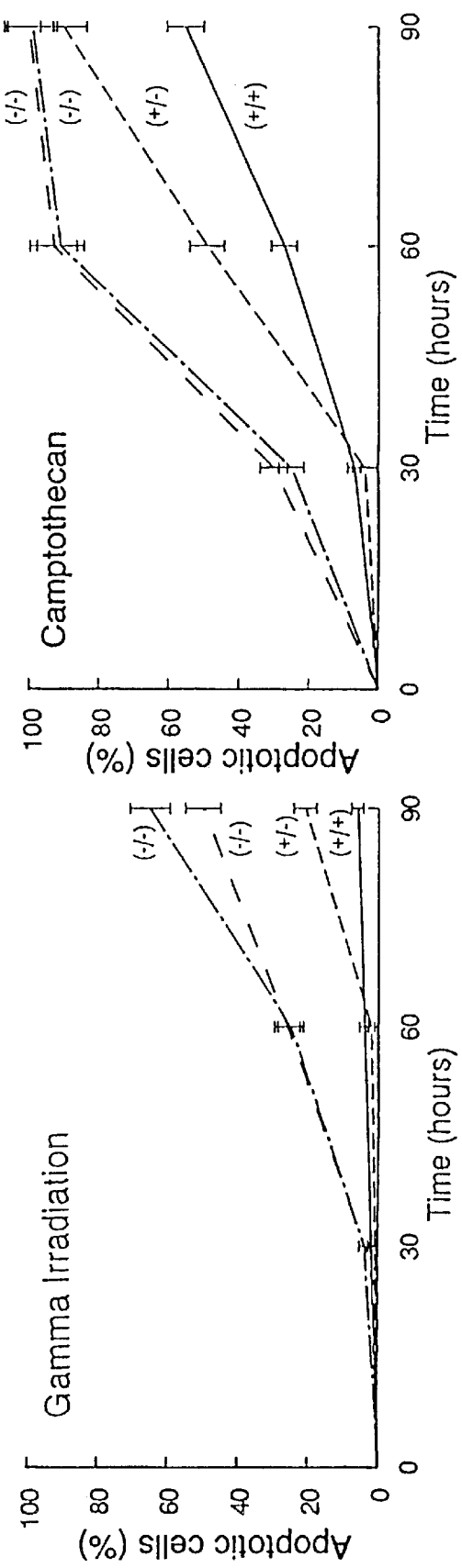
FIG. 2d

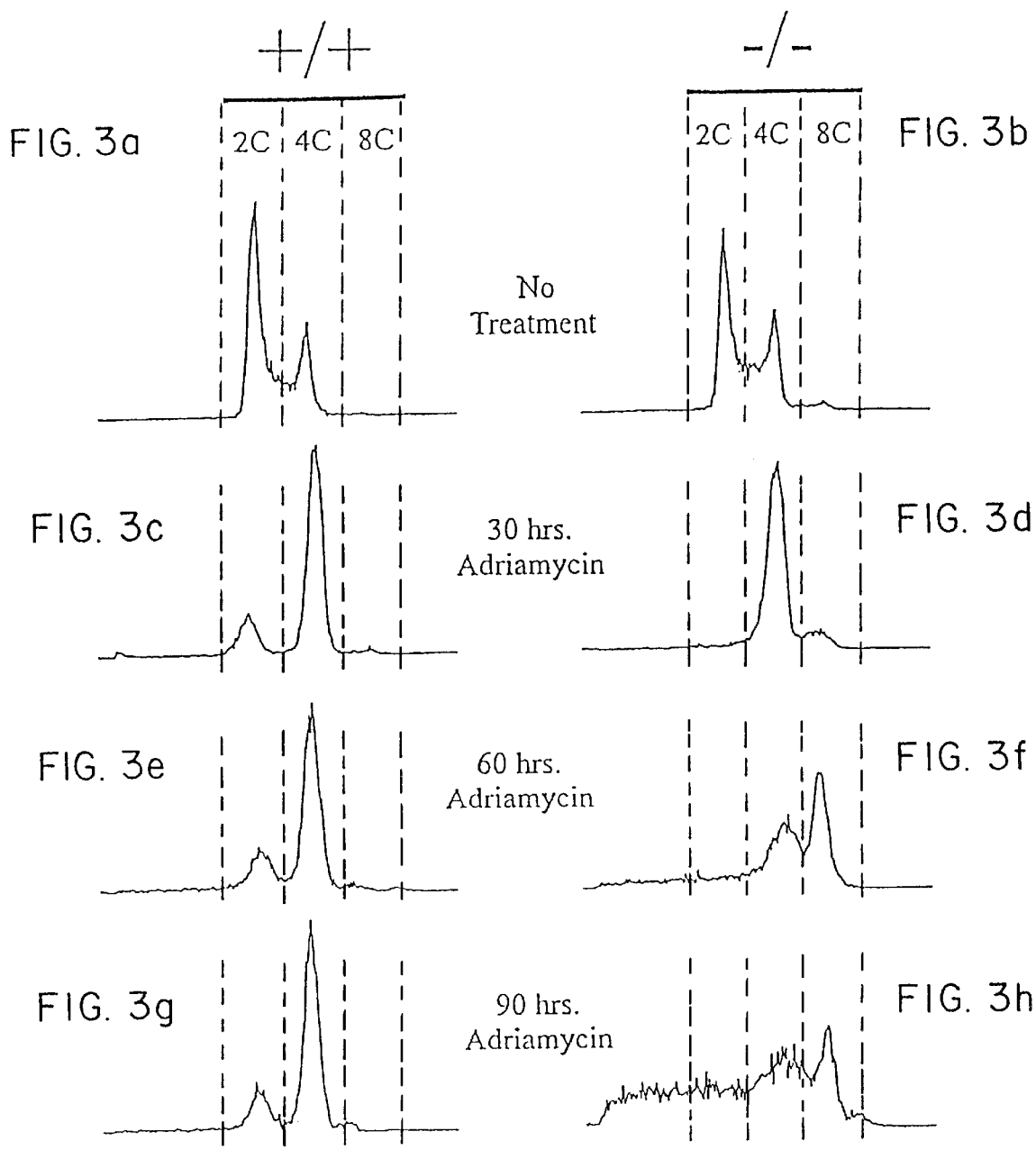

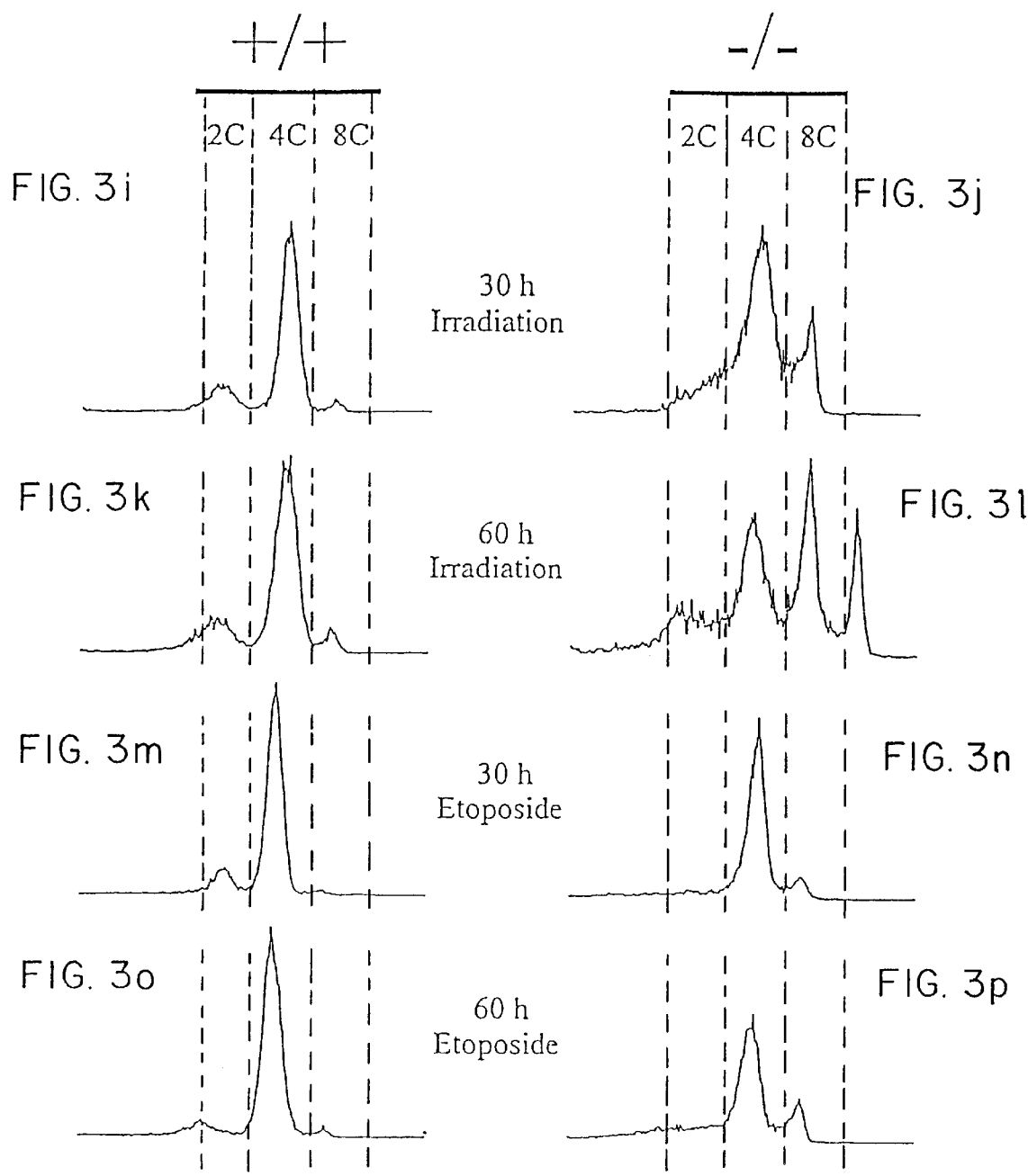

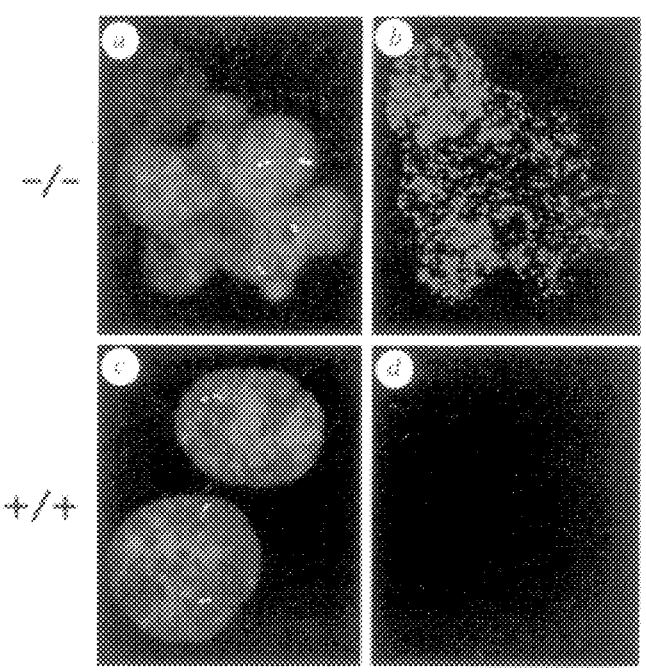

CANCER DRUG SCREEN BASED ON CELL CYCLE UNCOUPLING

This application is a division of application Ser. No. 08/620,340, filed Mar. 22, 1996.

This invention was made using U.S. government grants from the NIH CA43460, CA62924, CA35494, GM07309, and GM07184. Therefore the U.S. government retains certain rights to the invention.

BACKGROUND OF THE INVENTION

Precise coordination of the S and M phases of the eukaryotic cell cycle is critical not only for normal cell division, but also for effective growth arrest under conditions of stress. When damaged, a cell must communicate signals to both the mitotic and DNA synthesis machineries so that a mitotic block is not followed by an extra S phase, or vice versa. The biochemical mechanisms regulating this coordination, termed checkpoints, have been identified in lower eukaryotes, but are largely unknown in mammalian cells[1-3].

DNA-damaging agents are used in the clinic to preferentially kill cancer cells. However, there is a need in the art to discover additional therapeutic agents which are selectively toxic to cancer cells.

SUMMARY OF THE INVENTION

It is an object of the invention to provide methods for screening for anti-cancer drugs.

It is another object of the invention to provide cell lines useful for screening for anti-cancer drugs.

These and other objects of the invention are provided by one or more of the embodiments described below. In one embodiment of the invention, a method for screening test compounds to identify those which are potential anti-tumor agents is provided. The method comprises the steps of: determining DNA content of checkpoint gene-defective human cells incubated in the presence and in the absence of a test compound, wherein a test compound which causes DNA accumulation in the checkpoint gene-defective cell is identified as a potential anti-tumor agent.

In another embodiment of the invention, a different method of screening for potential anti-tumor agents is provided. The method comprises the steps of: determining viability or apoptosis of checkpoint gene-defective human cells incubated in the presence and in the absence of a test compound; selecting a test compound which causes cell death or apoptosis in the checkpoint gene-defective cell.

In yet another embodiment of the invention a homozygous checkpoint gene-defective human cell line is provided.

In still another embodiment of the invention a pair of isogenic cell lines is provided. The first cell line is a homozygous checkpoint gene-defective human cell line and the second cell line is a homozygous checkpoint gene-normal human cell line.

These and other embodiments of the invention provide the art with new methods and cell lines for screening potential anti-tumor agents.

BRIEF DESCRIPTION OF THE DRAWINGS

FIGS. 1A–1F The file if this patent contains at least one drawing executed in color show apoptosis in p21-deficient cells. Cells were grown for 90 hours in the presence of adriamycin and viewed with phase contrast microscopy (1a), after staining with the DNA-binding dye H33258 (1b), or after staining with the TUNEL assay to detect fragmented DNA (1c).

FIGS. 2A–2D demonstrate the kinetics of apoptosis following treatment of p21deficient cells with drugs or irradiation. Cells were treated with adriamycin (0.2 ug/ml), etoposide (5 ug/ml), or camptothecan (0.1 ug/ml), or gamma irradiated (12 Gy). At the indicated times, cells were harvested, stained with the DNA-binding dye H33258, and viewed by fluorescence microscopy to determine the fraction of apoptotic cells.

FIGS. 3A–3P show cell cycle analysis of drug treated cells. Cells with or without intact p21 genes were stained following various periods of drug treatment and examined by flow cytometry. The cells were untreated (FIGS. 3a, and 3b), treated with adriamycin (FIGS. 3c,3d, 3e, 3f, 3g, and 3h) or etoposide (FIGS. 3m, 3n, 3o, and 3p) for the indicated time periods, or treated with gamma irradiation and examined 30–60 hours later (FIGS. 3i, 3j, 3k, and 3l).

FIGS. 4A–4D demonstrate DNA synthesis and fluorescence in situ hybridization in p21-deficient and p21-positive cells. Cells without (4a, 4b) or with (4c, 4d) intact p21 genes were treated with adriamycin, pulse-labeled with BrdU to assess DNA synthesis, fixed and hybridized with a chromosome 3 probe by FISH (4a, 4c), then stained with the DNA-binding dye DAPI (4a, 4c) and anti-BrdU antibodies (4b, 4d). Hybridization signals from FISH are visualized as white dots, while nuclear morphology is revealed by the blue DAPI stain. Note that a single, lobulated nucleus is shown in 4a and 4b.

DETAILED DESCRIPTION OF THE INVENTION

It is a discovery of the present inventors that checkpoint gene-defective human cells are particularly useful for screening potential anti-tumor agents. This discovery is based on the observation that agents which are already known in the art to be particularly effective anti-tumor agents have a pronounced and detectable physiological effect on cells which are checkpoint gene-defective, e.g., p21-negative. In the absence of a functional cell cycle checkpoint, DNA-damaged cells arrest in G2 but then undergo additional S phases without intervening normal mitoses. They thereby acquire grossly deformed, polyploid nuclei and subsequently die through apoptosis.

According to the present invention, potential therapeutic agents are screened for the ability to cause DNA accumulation or cell death in checkpoint gene-defective human cells. Preferably, agents are screened for the ability to preferentially cause DNA accumulation or cell death in checkpoint gene-defective human cells as compared to checkpoint gene-normal human cells. More preferably, agents are screened for the ability to cause DNA accumulation to at least four times the haploid DNA content of the checkpoint gene-defective human cells.

A checkpoint gene is a gene whose product is involved in regulation of transitions between different cell cycle phases. Examples of such transitions or checkpoints are the initiation and the completion of DNA replication (S phase) and of cell division (M phase). Several checkpoints are regulated by a family of protein kinases, the CDKs, and their obligate activating partners, the cyclins. Deregulation of a transition occurs as a consequence of either the aberrant expression of positive regulators, such as the cyclins, or the loss of negative regulators, such as the CDK inhibitors, e.g., p21, p16, p15, p27 and p53. Any gene encoding positive or negative regulators of cell cycle checkpoints is a checkpoint gene and is contemplated for use in the present invention. In particular, genes encoding CDK inhibitors, e.g., p21, p16, p15, p27, and p53 are preferred. A checkpoint gene-defective cell is one which lacks one or two wild-type checkpoint gene alleles or is deficient in a checkpoint gene function. The defects may be due to abnormal expression of a checkpoint gene or mutation in a checkpoint gene. In a preferred embodiment, a checkpoint gene-defective cell lacks both wild-type checkpoint gene alleles, i.e., is homozygous.

Any means known in the art to generate a cell line which is defective in a known checkpoint gene can be used to obtain the checkpoint gene-defective cells. For example, a colonic cell line can be used to give rise to an isogenic p21-negative colonic cell line by promoterless homologous recombination[5]. The disclosure of reference 5 is expressly incorporated herein. A cell with two wild-type alleles of a checkpoint gene is a checkpoint gene-normal cell, for purposes of the present invention. Preferably, the checkpoint gene-defective cell used in the assay is the same type of cell (organ source) as the checkpoint gene-defective cell. More preferably the two cell lines are isogenic.

The DNA content of a cell incubated in the presence or absence of a test compound can be determined by any means known in the art. A DNA-binding dye may be employed to measure the DNA content. Procedures are available in the art to harvest cells, stain them with a DNA-binding dye, e.g., propidium iodide or H33258, and measure the incorporation of the DNA-binding dye by flow cytometry. Flow cytometry provides an ordinary artisan with information on the percentage of cells in a tested population with a diploid DNA content (2C), four times of haploid (4C), eight times of haploid (8C), etc. Alternatively, the DNA content of a cell can be determined by fluorescence in situ hybridization (FISH). Cells can be harvested, fixed on a slide, and hybridized with a chromosome probe. The DNA probe can be labeled and detected under fluorescence microscopy by any means known in the art. In one particular method, the DNA probe is biotinylated by nick translation and detected with fluorescein isothiocyanate (FITC) conjugated to avidin. The DNA content of a cell can be obtained by quantifying the intensity of the fluorescein signal through digital image acquisition and processing, which are readily available in the art.

It is well known in the art that viability of a cell can be determined by contacting the cell with a dye and viewing it under a microscope. Viable cells can be observed to have an intact membrane and do not stain, whereas dying or dead cells having "leaky" membranes do stain. Incorporation of the dye by the cell indicates the death of the cell. The most common dye used in the art for this purpose is trypan blue. Viability of cells can also be determined by detecting DNA synthesis. Cells can be cultured in cell medium with labeled nucleotides, e.g., $^3$H thymidine. The uptake or incorporation of the labeled nucleotides indicates DNA synthesis. In addition, colones formed by cells cultured in medium indicate cell growth and is another way to test viability of the cells.

Apoptosis is a specific mode of cell death recognized by a characteristic pattern of morphological, biochemical, and molecular changes. Cells going through apoptosis appear shrunken, and rounded; they also can be observed to become detached from culture dish. The morphological changes involve a characteristic pattern of condensation of chromatin and cytoplasm which can be readily identified by microscopy. When stained with a DNA-binding dye, e.g., H33258, apoptotic cells display classic condensed and punctate nuclei instead of homogeneous and round nuclei.

A hallmark of apoptosis is endonucleolysis, a molecular change in which nuclear DNA is initially degraded at the linker sections of nucleosomes to give rise to fragments equivalent to single and multiple nucleosomes. When these DNA fragments are subjected to gel electrophoresis, they reveal a series of DNA bands which are positioned approximately equally distant from each other on the gel. The size difference between the two bands next to each other is about the length of one nucleosome, i.e., 120 base pairs. This characteristic display of the DNA bands is called a DNA ladder and it indicates apoptosis of the cell. Apoptotic cells can be identified by flow cytometric methods based on measurement of cellular DNA content, increased sensitivity of DNA to denaturation, or altered light scattering properties. These methods are well known in the art and are within the contemplation of the invention.

Abnormal DNA breaks are also characteristic of apoptosis and can be detected by any means known in the art. In one preferred embodiment, DNA breaks are labeled with biotinylated dUTP (b-dUTP). Cells are fixed and incubated in the presence of biotinylated dUTP with either exogenous terminal transferase (terminal DNA transferase assay; TdT assay) or DNA polymerase (nick translation assay; NT assay). The biotinylated dUTP is incorporated into the chromosome at the places where abnormal DNA breaks are repaired, and are detected with fluorescein conjugated to avidin under fluorescence microscopy.

The following examples are provided for exemplification purposes only and are not intended to limit the scope of the invention which has been described in broad terms above.

EXAMPLE 1

Apoptosis In p21-Deficient Cells

HCT116 cells with (+/+) or without (−/−) p21 genes were generated by homologous recombination. Logarithmically-growing cells in McCoy's 5A medium with 10% fetal calf serum were treated with Adriamycin (0.2 ug/ml) for 90 hours. In FIG. 1b, the adherent cells were harvested by trypsinization and combined with cells floating in the media. After washing with Hanks Buffered Saline (HBS; Life Technologies), cells were resuspended in 40 ul HBS and added to 360 ul of a solution containing 0.7% NP-40, 4.7% formaldehyde and 11 ug/ml H33258 in phosphate buffered saline (PBS). Cells were then viewed under UV excitation and photographed with a Nikon Labophot microscope. In FIG. 1c, adherent cells were fixed in 1% formaldehyde, then incubated in the presence of exogenous terminal transferase and biotin-11-dUTP as previously described[7]. Labeled cells were detected by immunoperoxidase staining (Vector).

When treated with Adriamycin, the parental (p21$^{+/+}$) cells remained attached to the plate and appeared morphologically normal, as do other colorectal epithelial cell lines which growth arrest following DNA damage[3]. In contrast, the p21-deficient cells (p21$^{-/-}$) shrank, rounded, and detached from the dish, suggesting apoptosis (FIGS. 1a and 1b). To confirm this suggestion, cells were stained with the DNA-binding dye H33258, revealing a classic condensed and punctate nuclear morphology in the p21$^{-/-}$ cells, while the p21$^{+/+}$ cell nuclei were homogeneous and round (FIGS. 1c and 1d). The condensed, punctate nuclei were stained intensely by TUNEL[6,7], which detects the presence of DNA breaks characteristic of apoptosis (FIGS. 1e and 1f).

EXAMPLE 2

Kinetics of Apoptosis Following the Treatment of p21-Deficient Cells with Drugs or Irradiation Cells were grown, fixed, and stained as described in Example 1. Irradiation was delivered at 1 Gy/minute using a $^{137}$Cs source. Apoptotic cells were recognized as condensed, punctate nuclei (examples in FIG. 1d) or ghosts with faintly stained, degrading nuclei. At least 200 cells were counted for each time point, and the experiment was repeated with results virtually identical to those shown. The error bars represent the Poisson standard deviation determined by talking the square root of counted events and converting it to percent abundance. All counting was done in a blinded fashion. The (+/−) cells contained one normal p21 allele and one allele deleted by homologous recombination[5].

Time course analyses demonstrated that apoptosis was complete between 60 and 90 hours following Adriamycin treatment (FIG. 2a). The response to Adriamycin was found to be identical in a second, independently isolated p21$^{-/-}$ clone (FIG. 2a).

To determine whether these observations were generalizable with respect to DNA-damaging agents, we treated the cells with the topoisomerase II inhibitor etoposide, gamma irradiation, and the topoisomerase I inhibitor camptothecan. After etoposide or irradiation, the parental p21$^{+/+}$ cells remained healthy while their p21$^{-/-}$ derivatives died, as judged both by phase contrast microscopy and H33258 staining (FIGS. 2b, 2c, and 2d). With camptothecan, the parental p21$^{+/+}$ cells eventually underwent apoptosis, but this was significantly delayed compared to p21-deficient cells (FIG. 2d). Cells with one normal copy of p21 and one deleted copy (p21$^{+/-}$) behaved similarly to the parental cells after treatment with Adriamycin and etoposide (FIGS. 2a, and 2b), while treatment with camptothecan or gamma irradiation revealed a heterozygote effect (FIGS. 2c, and 2d).

EXAMPLE 3

Cell Cycle Analysis of Drug-Treated Cells

Cell growth, drug treatment, fixation, and staining with H33258 was performed as described in Example 2. Flow cytometry was performed as previously described[5].

Flow cytometry demonstrated that specific cell cycle changes were associated with this apoptotic process. Following 30 hours of exposure to Adriamycin, p21$^{+/+}$ cells were blocked in G1 and G2 phases, with few cells in S (FIG. 3c). In contrast, no G1 block was evident in the p21$^{-/-}$ cells[5], so that a nearly pure population of G2-arrested cells was observed (FIG. 3d). With longer treatments, the flow cytometry profile of p21$^{+/+}$ cells remained largely unchanged (FIGS. 3e, and 3g), indicating a stable growth arrest[8], while the p21$^{-/-}$ cells began to accumulate DNA in excess of 4C, then died (FIGS. 3f, and 3h). These characteristic changes— abnormally high DNA content coupled with apoptosis— were observed in p21$^{-/-}$ cells following treatment with each of the DNA-damaging drugs (examples in FIGS. 3f, 3h, 3n, 3p). Following gamma irradiation, there was a particularly striking accumulation of polyploid cells, with 33% and 15% of nuclei exhibiting DNA contents of 8C and 16C, respectively (FIG. 3l).

EXAMPLE 4

DNA Synthesis and Fluorescence in situ Hybridization in p21-Deficient Cells

Cells were grown and treated with Adriamycin as described in Example 1. After 60 hours of incubation, the cells were pulse-labeled with BrdU (5 uM) for 1.5 hours. The cells were then harvested, fixed on glass slides with methanol:acetic acid (3:1), treated with RNAse and pepsin[28], and FISH performed[29] with a P1 clone derived from 3p21.1-3. The P1 probe DNA was biotinylated by nick translation and detected with fluorescein isothiocyanate (FITC) conjugated to avidin[30]. BrdU incorporation was detected by indirect immunofluorescence using an anti-BrdU antibody (5 ug/ml, Pharmingen) and an anti-mouse IgG TRITC conjugate (Sigma). Cells were counterstained with 0.1 ug/ml DAPI. Photographs were taken using a CCD camera (Photometrics) after digital image acquisition and processing as described previously[29].

Previous studies have suggested that nuclei do not re-enter S phase during a block in G2 or M due either to the absence of required (positive) effectors or to the presence of negative effectors[1–3]. Our studies clearly show that a major effector of this M/S coupling in HCT116 cells is negative and identify it as p21. The p21 protein could achieve its effect by inhibiting cyclin-cdk complexes or by inhibiting proliferating cell nuclear antigen, a polymerase processivity factor required for DNA replication[9,10]. The lack of inhibition of cyclin-cdk complexes could also promote the subsequent apoptosis[11–14]. The effects of p21 deletion described here are in some ways different from those caused by deletion of p21 in mouse fibroblasts[15,16]. Whether such differences reflect cell type or species-specific factors is unclear; it is known that the control of S/M coupling is heterogeneous, differing significantly, for example, between different mammalian cell types[17,18] and between fission yeast and budding yeast[2].

The data also demonstrate that the absence of p21 renders cells remarkably sensitive to apoptosis following treatment with several cancer therapeutics. The cellular events accompanying this sensitivity appear uniform-cells initiate and often complete entire rounds of DNA synthesis in the absence of mitosis, leading to gross nuclear abnormalities followed by programmed cell death. These results provide experimental evidence for the hypothesis that disruption of checkpoint function could make mammalian cells more sensitive to chemotherapeutic agents[1–3,18,19]. They also have potential implications for understanding the successes and failures of current cancer therapy, as naturally occurring cancers often have alterations of cyclins, cdk's, or cdk inhibitors (including p21) which could make them functionally equivalent to p21$^{-/-}$ cells[20–22]. The data also suggest that the sensitivity of a cell to chemotherapeutic agents and irradiation will depend on the relative intactness of both its M/S coupling and apoptotic controls[17,23]. This may explain why p53-deficient cells are relatively resistant to cancer drugs[24], as their apoptotic response is abnormal[24–27], unlike that in p21-deficient cells[15,16].

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

REFERENCES

1. Murray, A. W. *Nature* 359, 599–604 (1992).
2. Nurse, P. *Cell* 79, 547–550 (1994).
3. Hartwell, L. H. & Kastan, M. B. *Science* 266, 1821–1828 (1994).
4. Nasmyth, K. & Hunt, T. *Nature* 366, 634–635 (1993).
5. Waldman, T., Kinzler, K. W. & Vogelstein, B. *Cancer Res.* 55, 5187–5190 (1995).
6. Gavrieli, Y., Sherman, Y. & Ben-Sasson, S. A. *J. Cell Biol.* 119, 493–501 (1992).

7. Gorczyca, W., Gong, J. & Darzynkiewicz, Z. *Cancer Res.* 53, 1945–1951 (1993).
8. Di Leonardo, A. et al. *Genes and Development* 8, 2540–2551 (1994).
9. Waga, S. Hannon, G. J., Beach, D. & Stillman, B. *Nature* 369, 574–578 (1994).
10. Flores-Rozas, H. et al. *Proc. Natn. Acad. Sci. U.S.A.* 91, 8655–8699 (1994).
11. Heald, R., McLoughlin, M. & McKeon, F. *Cell* 74, 463–474 (1993).
12. Meikrantz, W., Gisselbrecht, S. , Tam, S. W., and Schlegel, R. *Proc. Natn. Acad. Sci. U.S.A.* 91, 3754–3758 (1994).
13. Hoang, A. T et al. *Proc. Nat. Acad. Sci. U.S.A.* 91, 6875–6879 (1994).
14. Shi, L. et al. *Science* 263, 1143–1145 (1994).
15. Deng, C. et al. *Cell* 82, 675–684 (1995).
16. Brugarolas, J. et al. *Nature* 377, 552–557 (1995).
17. Woods, C. M. et al. *Molecular Medicine* 1, 506–526 (1995).
18. Kung, A. L., Sherwood, S. W., and Schimke, R. T. *Proc. Natn. Acad. Sci. U.S.A.* 87: 9553–9557 (1990).
19. Kung, A. L., Zetterberg, A., Sherwood, S. W. & Schimke, R. T. *Cancer Res.* 50, 7307–7317 (1990).
20. Gao, X. et al. *Oncogene* 11, 1395–1398 (1995).
21. Hunter, T. & Pines, J. *Cell* 79, 573–582 (1994).
22. Sherr, C. J. & Roberts, J. M. *Genes and Development* 9: 1149–1163 (1995).
23. Cross, S. M. et al. *Science* 267, 1353–1356 (1995).
24. Lowe, S. W. et al. *Cell* 74, 957–967 (1993).
25. Yonish-Rouach, E. et al. *Nature* 352, 345–7 (1991).
26. Lowe, S. W. et al. *Nature* 362, 847–849 (1993).
27. Clarke, A. R. et al. *Nature* 362, 849–852 (1993).
28. Ried, T. et al. *Genes, Chromosomes, & Cancer* 4, 69–74 (1992).
29. Lengauer, C. et al. *Genetic Analysis Techniques and Applications* 11, 140–147 (1994).
30. Lichter, P. & Cremer, T. *Human Cytogenetics:A Practical Approach,* 157–192 (Oxford, IRL University Press, 1992).

We claim:

1. A method for screening test compounds to identify those which are potential anti-tumor agents, comprising the steps of:

determining DNA content of p21 checkpoint gene-defective human colonic cells incubated in the presence and in the absence of a test compound, wherein a test compound which causes DNA accumulation in the checkpoint gene-defective cells is identified as a potential anti-tumor agent.

2. The method of claim 1 wherein the DNA accumulation is in excess of four times the cells' haploid DNA content.

3. The method of claim 1 wherein the DNA content of the cells is determined by staining the cells with a DNA-binding dye.

4. The method of claim 3 wherein the DNA-binding dye is selected from the group consisting of H33258 and propidium iodide.

5. The method of claim 3 further comprising measuring the incorporation of the DNA-binding dye by flow cytometry.

6. The method of claim 1 wherein the DNA content of the cells is determined by fluorescence in situ hybridization (FISH).

7. The method of claim 1 further comprising the steps of:

determining DNA content of p21 checkpoint gene-normal human colonic cells incubated in the presence and in the absence of the potential anti-tumor agent;

identifying a potential anti-tumor agent which preferentially causes DNA accumulation in the checkpoint gene-defective cells as compared to the checkpoint gene-normal cells.

8. The method of claim 7 wherein the DNA accumulation is in excess of four times haploid DNA content of the checkpoint gene-defective cells in the absence of the test compound.

9. The method of claim 7 wherein the DNA content of the cells is determined by staining the cell with a DNA-binding dye.

10. The method of claim 9 wherein the DNA-binding dye is selected from the group consisting of H33258 and propidium iodide.

11. The method of claim 9 further comprising measuring the incorporation of the DNA-binding dye by flow cytometry.

12. The method of claim 7 wherein the DNA content of the cells is determined by fluorescence in situ hybridization (FISH).

* * * * *